United States Patent
Kang et al.

(10) Patent No.: US 11,234,647 B2
(45) Date of Patent: Feb. 1, 2022

(54) BIO-INFORMATION MEASURING APPARATUS AND BIO-INFORMATION MEASURING METHOD

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 164 days.

(21) Appl. No.: 16/268,072

(22) Filed: Feb. 5, 2019

(65) Prior Publication Data
US 2020/0037956 A1 Feb. 6, 2020

(30) Foreign Application Priority Data
Aug. 1, 2018 (KR) .................. 10-2018-0089784

(51) Int. Cl.
*A61B 5/00* (2006.01)
*G06K 9/00* (2006.01)
(Continued)

(52) U.S. Cl.
CPC .......... *A61B 5/6843* (2013.01); *A61B 5/0205* (2013.01); *A61B 5/02007* (2013.01); *A61B 5/1172* (2013.01); *A61B 5/165* (2013.01); *G06K 9/0002* (2013.01); *A61B 5/02108* (2013.01); *A61B 5/02427* (2013.01)

(58) Field of Classification Search
CPC .......... A61B 5/02108; A61B 5/1172; A61B 5/02416; A61B 5/02433; A61B 2562/0214
See application file for complete search history.

(56) References Cited

U.S. PATENT DOCUMENTS 6,459,804 B2 10/2002 Mainguet
7,598,878 B2 10/2009 Goldreich
(Continued)

FOREIGN PATENT DOCUMENTS

EP    3 342 336 A1    7/2018
KR    10-2006-0081178 A    7/2006
(Continued)

OTHER PUBLICATIONS

Anand Chandrasekhar et al., "Smartphone-based blood pressure monitoring via the oscillometric finger-pressing method", Science Translational Medicine, vol. 10, No. 431, XP055463286, Mar. 7, 2018, 12 pages.
(Continued)

*Primary Examiner* — Gary Jackson
*Assistant Examiner* — Zahed Kabir
(74) *Attorney, Agent, or Firm* — Sughrue Mion, PLLC

(57) ABSTRACT

An apparatus for measuring bio-information such as blood pressure is provided. The bio-information measuring apparatus includes: a pulse wave sensor configured to measure a pulse wave signal from an object; a fingerprint sensor configured to obtain fingerprint information of the object; and a processor configured to estimate a contact area of the object based on the fingerprint information, and obtain bio-information based on the pulse wave signal and the contact area.

11 Claims, 21 Drawing Sheets

(51) Int. Cl.
  *A61B 5/1172* (2016.01)
  *A61B 5/0205* (2006.01)
  *A61B 5/02* (2006.01)
  *A61B 5/16* (2006.01)
  *A61B 5/021* (2006.01)
  *A61B 5/024* (2006.01)

(56) References Cited

U.S. PATENT DOCUMENTS

| | | |
|---|---|---|
| 8,313,439 B2 | 11/2012 | McCombie et al. |
| 9,529,436 B2 | 12/2016 | Lee et al. |
| 9,974,482 B2 | 5/2018 | Shim et al. |
| 2006/0020216 A1 | 1/2006 | Oishi et al. |
| 2007/0299322 A1* | 12/2007 | Miyajima ............ H04M 1/0202 600/301 |
| 2015/0062078 A1 | 3/2015 | Christman et al. |
| 2015/0230761 A1 | 8/2015 | Brumback et al. |
| 2016/0139668 A1 | 5/2016 | Lee et al. |
| 2016/0173886 A1* | 6/2016 | Bae .................... H04N 19/147 382/166 |
| 2017/0095168 A1 | 4/2017 | Kwon et al. |
| 2017/0109495 A1 | 4/2017 | Xin |
| 2017/0119307 A1 | 5/2017 | Shim et al. |
| 2017/0224236 A1 | 8/2017 | Ho et al. |
| 2018/0177413 A1 | 6/2018 | Kwon et al. |
| 2018/0300526 A1* | 10/2018 | Cho ..................... G06F 3/042 |
| 2018/0344193 A1* | 12/2018 | Gui ...................... A61B 5/282 |
| 2019/0059751 A1* | 2/2019 | Huang ............... A61B 5/02108 |

FOREIGN PATENT DOCUMENTS

| | | |
|---|---|---|
| KR | 10-1559288 B1 | 10/2015 |
| KR | 10-2017-0040034 A | 4/2017 |
| KR | 10-2017-0049280 A | 5/2017 |

OTHER PUBLICATIONS

Communication dated May 7, 2019, issued by the European Patent Office in counterpart European Application No. 19161830.5.

\* cited by examiner

FIG. 7B

| | | | 6 | 6 | 6 | 6 | | | |
|---|---|---|---|---|---|---|---|---|---|
| | | 7 | 8 | 8 | 8 | 8 | 7 | | |
| | 7 | 8 | 9 | 9 | 9 | 9 | 8 | 7 | |
| 6 | 8 | 9 | 10 | 10 | 11 | 10 | 9 | 8 | 7 |
| 7 | 8 | 10 | 11 | 12 | 13 | 12 | 11 | 9 | 8 |
| 7 | 8 | 10 | 12 | 13 | 15 | 13 | 12 | 10 | 8 |
| 7 | 8 | 10 | 12 | 13 | 15 | 13 | 12 | 10 | 8 |
| 6 | 8 | 10 | 11 | 12 | 13 | 13 | 12 | 10 | 8 |
| 6 | 8 | 9 | 10 | 11 | 12 | 12 | 11 | 9 | 8 |
| | 7 | 8 | 10 | 10 | 10 | 10 | 10 | 9 | 8 |
| | 7 | 8 | 9 | 9 | 9 | 9 | 9 | 8 | 7 |
| | | 7 | 8 | 8 | 8 | 8 | 8 | 7 | |

—A2

BIO-INFORMATION MEASURING APPARATUS AND BIO-INFORMATION MEASURING METHOD

CROSS-REFERENCE TO RELATED APPLICATION(S)

This application claims priority from Korean Patent Application No. 10-2018-0089784, filed on Aug. 1, 2018, in the Korean Intellectual Property Office, the disclosure of which is incorporated herein by reference in its entirety.

BACKGROUND

1. Field

Apparatuses and methods consistent with exemplary embodiments relate to measuring bio-information, and more particularly to cufflessly measuring blood pressure.

2. Description of the Related Art

As a method of measuring blood pressure in a non-invasive manner without causing pain or discomfort to a human body, there is a cuff-based measurement method for measuring blood pressure using cuff pressure measurements and a cuffless measurement method for estimating blood pressure using pulse wave measurements without a cuff.

As the cuff-based measurement method for measuring blood pressure, there is a Korotkoff-sound method which measures blood pressure by winding a cuff around an upper arm and hearing the sound of blood vessels through a stethoscope during inflation and deflation of the cuff; and an oscillometric method which measures blood pressure by winding a cuff around an upper arm and continuously measuring cuff pressure while inflating and then gradually deflating the cuff using an automated device, and measuring blood pressure based on a point of maximum pressure signal change.

As the cuffless measurement method for measuring blood pressure, there is a method of estimating blood pressure by calculating a Pulse Transit Time (PTT), and a Pulse Wave Analysis (PWA) method of estimating blood pressure by analyzing a pulse wave form.

SUMMARY

According to an aspect of an exemplary embodiment, there is provided a bio-information measuring apparatus including: a pulse wave sensor configured to measure a pulse wave signal from an object; a fingerprint sensor configured to obtain fingerprint information of the object; and a processor configured to estimate a contact area between the object and the pulse wave sensor based on the fingerprint information, and obtain bio-information based on the pulse wave signal and the contact area.

The pulse wave sensor may include: a light source configured to emit light onto the object; and a detector configured to detect the light that is reflected from the object after being emitted to the object.

The fingerprint sensor may be a capacitive fingerprint sensor.

The processor may be further configured to calculate a statistical value of pixel intensities included in the fingerprint information, and estimate the contact area from the statistical value by applying a contact area conversion function.

The processor may be further configured to determine a contact pressure between the pulse wave sensor and the object based on the contact area.

The processor may be further configured to determine force exerted from the object to the pulse wave sensor, and determine the contact pressure based on the force and the contact area.

The bio-information measuring apparatus may further include a force sensor configured to measure the force exerted to the pulse wave sensor.

The pulse wave sensor may measure a plurality of pulse wave signals of multiple wavelengths, and the processor is further configured to determine the force based on the plurality of pulse wave signals of the multiple wavelengths.

The pulse wave signal has a first wavelength, and the pulse wave sensor measures a plurality of pulse signals having two or more wavelengths different from the first wavelength. The processor may be further configured to obtain a differential signal between the pulse wave signal of the first wavelength and each of the plurality of pulse wave signals having the two or more wavelengths different from the first wavelength, and determine force exerted from the object to the pulse wave sensor based on the differential signal and the contact area.

The processor may be further configured to determine the contact pressure based on the contact area by applying a contact pressure conversion function.

The processor may be further configured to obtain an oscillometric waveform based on the plurality of pulse wave signals and the contact pressure, and obtain the bio-information based on the oscillometric waveform.

The processor may be further configured to provide a user with guide information including at least one of a reference contact position and a reference contact intensity of the object.

The processor may be further configured to determine a contact state between the object and the pulse wave sensor during measurement of the pulse wave signal based on a fingerprint image included in the fingerprint information.

The processor may be further configured to extract a fingerprint feature point from the fingerprint image, and determine the contact state based on a distance between the extracted fingerprint feature point and a center position of the fingerprint sensor.

In response to determining that the contact state being in an abnormal state, the processor may be further configured to provide guide information for guiding a user to change a contact position of the object.

The bio-information may include at least one of blood pressure, vascular age, degree of arteriosclerosis, aortic pressure waveform, vascular compliance, stress index, and degree of fatigue.

The processor may be further configured to determine a change in the contact area between the pulse wave sensor and the object while the pulse wave signal is being measured, and obtain the bio-information based on the pulse wave signal and the change in the contact area.

The fingerprint information may include pixel intensities. The processor may be further configured to estimate the contact area by linearly combining one or more of the pixel intensities which are equal to or higher than a predetermined threshold value.

According to an aspect of another exemplary embodiment, there is provided a bio-information measuring method including: obtaining a pulse wave signal from an object by using a pulse wave sensor; obtaining fingerprint information of the object; estimating a contact area between the object and the pulse wave sensor based on the fingerprint information; and obtaining bio-information based on the pulse wave signal and the contact area.

The estimating the contact area may include: calculating a statistical value of pixel intensities included in the fingerprint information; and estimating the contact area from the statistical value by applying a contact area conversion function.

The bio-information measuring method may further include determining a contact pressure between the object and the pulse wave sensor based on the contact area.

The bio-information measuring method may further include determining force exerted from the object to the pulse wave sensor. The determining the contact pressure may include determining the contact pressure based on the force and the contact area.

The determining the contact pressure signal may include determining the contact pressure signal based on the contact area by applying a contact pressure conversion function.

The obtaining the bio-information may include obtaining an oscillometric waveform based on the pulse wave signal and the contact pressure; and obtaining the bio-information based on the oscillometric waveform.

The bio-information measuring method may further include in response to receiving a request for measuring the bio-information, providing guide information which includes at least one of a reference contact position and a reference contact intensity.

The bio-information measuring method may further include determining a contact state between the object and the pulse wave sensor based on a fingerprint image included in the fingerprint information during measurement of the pulse wave signal.

The bio-information measuring method may further include in response to determining that the contact state being in an abnormal state, providing guide information for guiding a user to change a contact position of the object.

The bio-information measuring method may further include: determining a change in the contact area between the pulse wave sensor and the object while obtaining the pulse wave signal, wherein the obtaining the bio-information may include obtaining the bio-information based on the pulse wave signal and the change in the contact area.

The fingerprint information may include a fingerprint image, and the estimating the contact area may include: determining pixels of the fingerprint image which have intensities equal to or higher than a predetermined threshold value; and estimating the contact area by linearly combining the intensities of the determined pixels.

BRIEF DESCRIPTION OF THE DRAWINGS

The above and/or other aspects will be more apparent by describing certain exemplary embodiments, with reference to the accompanying drawings, in which:

FIGS. 7A and 7B are diagrams explaining an example of estimating a contact area according to the exemplary embodiment of FIG. 6;

DETAILED DESCRIPTION

Figure 1:
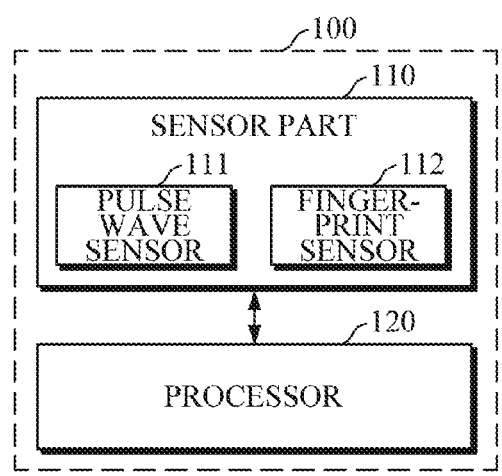
FIG. 1 is a block diagram illustrating a bio-information measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Various embodiments of the bio-information measuring apparatus which will be described below may be embedded in various devices such as a mobile wearable device, a smart device, and the like. Examples of the various devices may include a wearable device of various types such as a smart watch worn on the wrist, a smart band-type wearable device, a headphone-type wearable device, a hairband-type wearable device, and the like, a mobile device such as a smartphone, a tablet PC, and the like, but are not limited thereto.

Figure 2A:
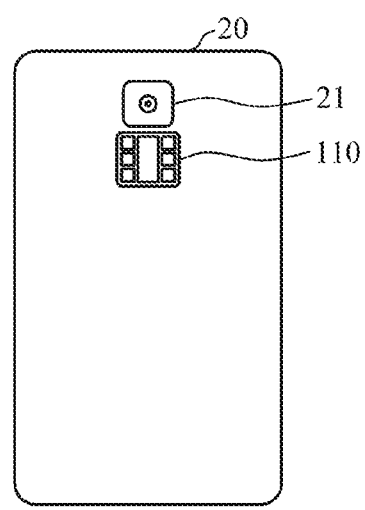
FIGS. 2A, 2B, and 2C are diagrams illustrating a sensor part according to an exemplary embodiment.
Figure 2B:
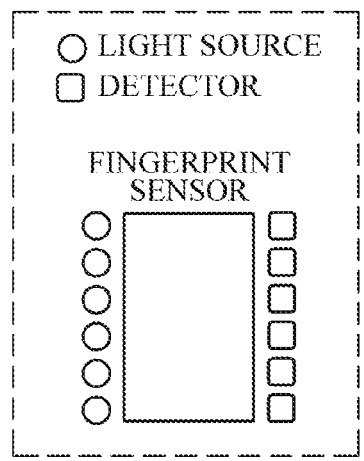
Figure 2C:
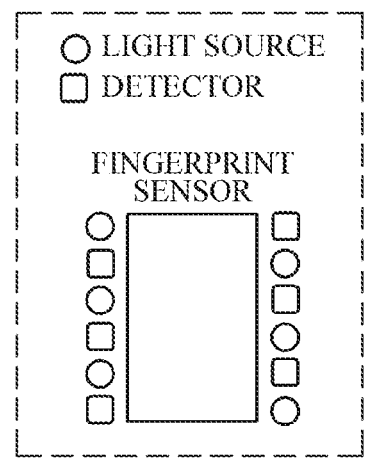

FIG. 1 is a block diagram illustrating a bio-information measuring apparatus according to an exemplary embodiment. FIGS. 2A to 2C are diagrams illustrating examples of a configuration of a sensor part of the bio-information measuring apparatus.

Referring to FIG. 1, the bio-information measuring apparatus 100 includes a sensor part 110 and a processor 120.

The sensor part 110 includes a pulse wave sensor 111 and a fingerprint sensor 112. The pulse wave sensor 111 may measure a pulse wave signal, including a photoplethysmography (PPG) signal, from an object. The pulse wave sensor 111 includes a light source which emits light onto an object, and a detector which detects light emitted by the light source and scattered or reflected from body tissues such as skin surface, vessels, and the like.

The light source may include a light emitting diode (LED), a laser diode (LD), a fluorescent body, and the like, but is not limited thereto. The detector may include a photo diode, a photo transistor (PTr), an image sensor (e.g., CMOS image sensor), and the like, but is not limited thereto. The pulse wave sensor 111 may include an array of a plurality of light sources and/or detectors if necessary. In particular, the plurality of light sources may emit light of different wavelengths, and may be spaced apart at different distances from the detector.

The fingerprint sensor 112 may obtain fingerprint sensor information from a user. In particular, the fingerprint sensor information may include information on each pixel intensity of the fingerprint sensor 112 which is measured when the user touches the fingerprint sensor 112 by using his/her finger or another body part. In one exemplary embodiment, the fingerprint sensor 112 may be a capacitive fingerprint sensor, but is not limited thereto. For convenience of explanation, the following description will be made by using a capacitive fingerprint sensor as an example.

In the case in which the fingerprint sensor 112 is a capacitive fingerprint sensor, each pixel intensity may refer to capacitance accumulated on each pixel. For example, when a finger of a user touches the sensor part 110 to measure bio-information, capacitance is accumulated on each pixel of the fingerprint sensor 112. The capacitance accumulated on each pixel is generally changed in response to a change in a duration and an area of contact between the finger and the fingerprint sensor 112.

FIG. 2A illustrates a rear surface of a smart device 20 including a bio-information measuring apparatus 100, according to an exemplary embodiment. The bio-information measuring apparatus 100 may include an image sensor 21 and a sensor part 11 disposed on the rear surface of the smart device 20. The image sensor 21 may capture an image of a user, and the sensor part 20 may include a fingerprint sensor 112. In FIG. 2A, the image sensor 21 and the sensor part 11 including the fingerprint sensor 112 are amounted on the rear surface, but the present exemplary embodiment is not limited thereto. For example, the fingerprint sensor 112 may be mounted at a front surface (e.g., at a lower front surface) of the smart device 20. In particular, the fingerprint sensor 112 may be disposed at the lower front surface, and the pulse wave sensor 111 may be disposed around the fingerprint sensor 112.

FIGS. 2B and 2C illustrate various examples of a structure of the sensor part 110. For example, as illustrated in FIG. 2B, the light source of the pulse wave sensor 111 is disposed at one side of the fingerprint sensor 112, and the detector may be disposed on the other side of the fingerprint sensor 112. In another example, as illustrated in FIG. 2C, the light source and the detector of the pulse wave sensor 111 may be disposed alternately on both sides of the fingerprint sensor 112. The fingerprint sensor 112 may be formed in various shapes such as a circular shape, a triangular shape, and the like. The pulse wave sensor 111 may be disposed equally on all sides of the fingerprint sensor 112. Alternatively, in the case in which the fingerprint sensor 112 is made of a light-transmitting material, the pulse wave sensor 111 may be disposed below the fingerprint sensor 112, in which the detector may be disposed at the center of the fingerprint sensor 112, and a plurality of light sources may be disposed around the detector.

The processor 120 controls the sensor part 110 in response to the request for measuring bio-information. The processor 110 may be electrically connected with the sensor part 110. The processor 120 may receive a pulse wave signal and fingerprint sensor information from the sensor part 120, and may measure bio-information based on the received pulse wave signal and fingerprint sensor information.

For example, upon receiving the fingerprint sensor information, the processor 120 may estimate a contact area between an object and the sensor part 110, by using each pixel intensity included in the fingerprint sensor information. Upon estimating the contact area, the processor 120 may measure bio-information based on the received pulse wave signal and the estimated contact area. In particular, the bio-information may include a heart rate, blood pressure, vascular age, arterial stiffness, aortic pressure waveform, vascular compliance, stress index, degree of fatigue, and the like, but is not limited thereto.

Figure 3:
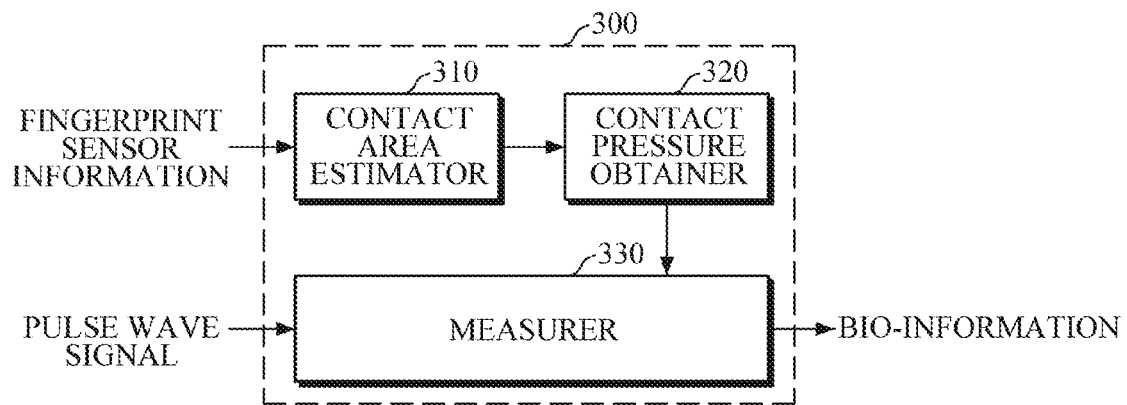
FIG. 3 is a diagram illustrating an example of a configuration of a processor of FIG. 1.
Figure 4A:
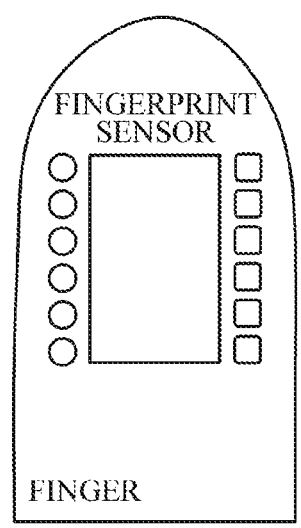
FIGS. 4A, 4B, 4C, and 4D are diagrams explaining an example of measuring bio-information according to an exemplary embodiment.
Figure 4B:
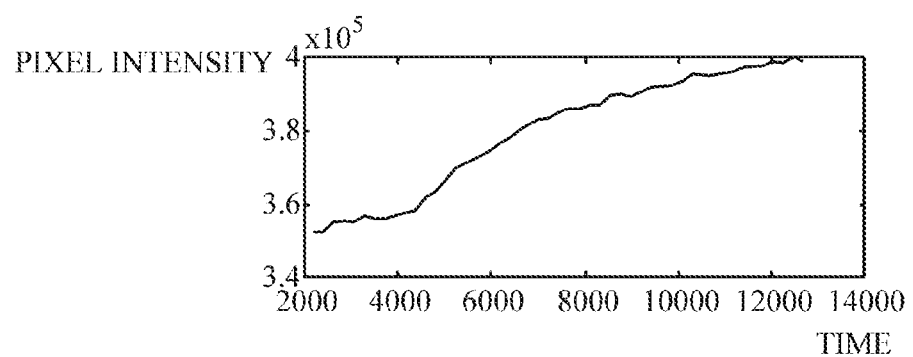
Figure 4B:
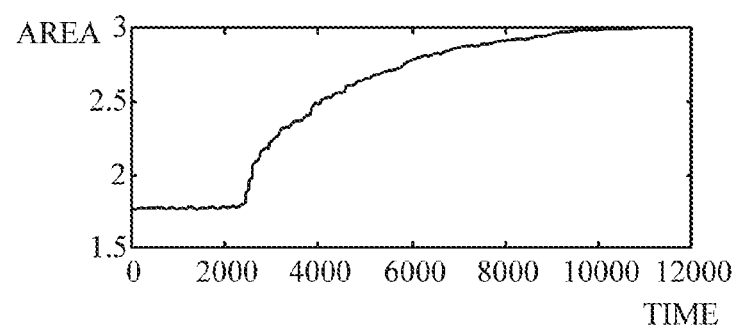

FIG. 3 is a diagram illustrating an example of a configuration of a processor of FIG. 1. FIGS. 4A to 4B are diagrams explaining an example of measuring bio-information.

Referring to FIG. 3, the processor 300 according to an exemplary embodiment includes a contact area estimator 310, a contact pressure obtainer 320, and a measurer 330.

As illustrated in FIG. 4A, once a finger touches the sensor part 110, the fingerprint sensor 112 obtains fingerprint sensor information and transmits the obtained fingerprint sensor information to the contact area estimator 310. Upon receiving the finger sensor information from the fingerprint sensor 112, the contact area estimator 310 may estimate a contact area of the finger by using the fingerprint sensor information.

FIG. 4B illustrates a relationship between a contact area increase and a pixel intensity increase. The contact area estimator 310 may estimate a contact area based on pixel intensity values included in the fingerprint sensor information. For example, the contact area estimator 310 may calculate a statistical value of each pixel intensity. In particular, the statistical value may be various values such as a simple sum, a weighted sum, an average, a median value, and the like of pixel intensities, but is not limited thereto. Upon calculating the statistical value, the contact area estimator 310 may calculate a contact area using the statistical value by applying a predefined contact area conversion function to the statistical value. In particular, the contact area conversion function may be defined as a linear/non-linear combination function, and the like.

Once the contact area is estimated, the contact pressure obtainer 320 may obtain a contact pressure signal between the object and the pulse wave sensor 111 from the estimated contact area. For example, when a user's finger touches the fingerprint sensor 112 with gradually increasing force, to increase contact pressure between the finger and the fingerprint sensor 112, the contact area becomes wider, such that it can be seen that there is a correlation between the contact area and the contact pressure. Accordingly, by applying a contact pressure conversion function which represents a correlation between the contact area and the contact pressure, the contact pressure obtainer 320 may obtain the contact pressure from the contact area. The contact pressure conversion function may be predefined as a linear/non-linear combination function.

Further, when a user's finger touches the sensor part 110 to measure bio-information, the pulse wave sensor 111 measures a pulse wave signal from the object. In particular, while the user's finger touches the sensor part 110, the user may gradually increase the contact pressure between the finger and the sensor part 110 by touching the sensor part 110 with gradually increasing force during measurement of bio-information. Alternatively, at the beginning of measurement of bio-information, when a user's finger touches the sensor 110 with a pressure intensity equal to or higher than a predetermined threshold, the user may gradually decrease the contact pressure between the finger and the sensor part 110 by touching the sensor part 110 with gradually decreasing force.

Once the contact pressure signal is obtained, the measurer 330 may measure bio-information based on the pulse wave signal and the contact pressure signal. For example, the measurer 330 may measure blood pressure by using an oscillometric method. The measurer 330 may obtain an oscillometric waveform by using the pulse wave signal and the contact pressure signal, and may measure bio-information by using the obtained oscillometric waveform.

Figure 4C:
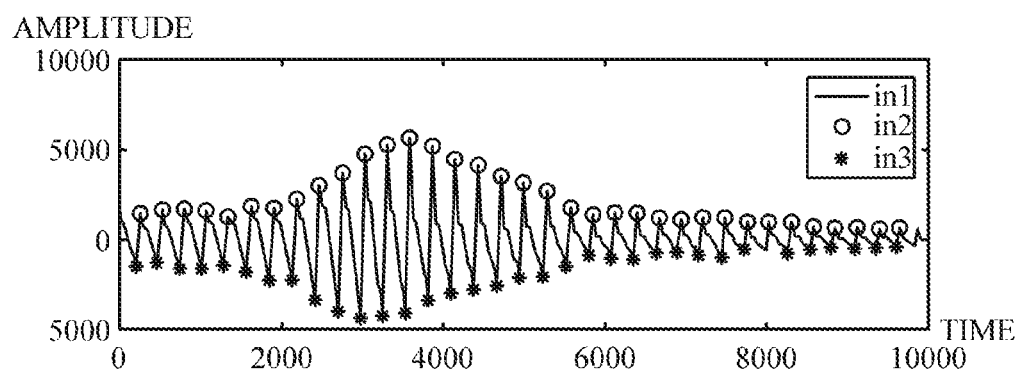
Figure 4D:
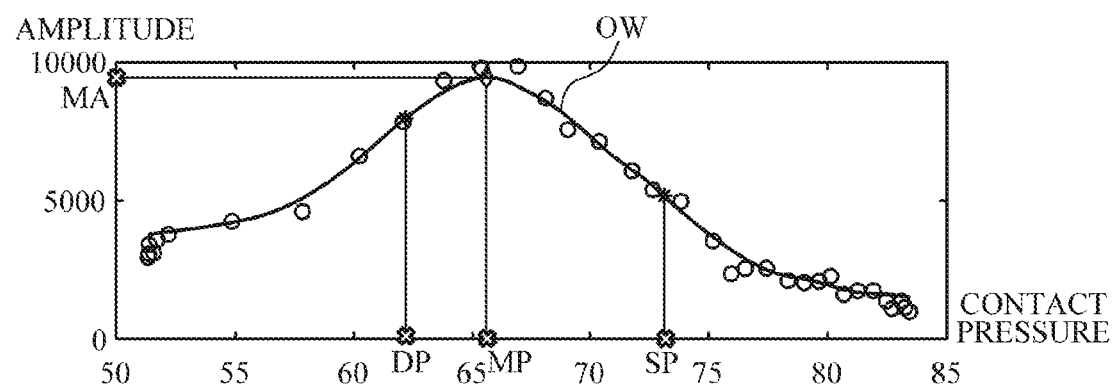

For example, the measurer 330 may extract a peak-to-peak point at each measurement point of the pulse wave signal, and may obtain the oscillometric waveform of a contact pressure versus pulse wave signal, by plotting the extracted peak-to-peak point based on a contact pressure value corresponding to each measurement point. Referring to FIG. 4C, a pulse wave signal is obtained by gradually increasing the contact pressure between the finger and the sensor part 110 or by gradually decreasing the contact pressure therebetween while a user touches the sensor part 110 with a pressure intensity equal to or higher than a predetermined threshold. The measurer 330 may extract the peak-to-peak point by subtracting an amplitude value in3 of a negative (−) point from an amplitude value in2 of a positive (+) point of the waveform envelope in1 at each measurement point of the obtained pulse wave signal. Then, as illustrated in FIG. 4D, the measurer 330 may obtain the oscillometric waveform (OW) by plotting the peak-to-peak amplitude at each measurement point based on the contact pressure value.

Upon obtaining the oscillometric waveform, the measurer 330 may extract one or more features from the obtained oscillometric waveform. Referring to FIG. 4D, the measurer 330 may extract, as features, an amplitude value MA of a maximum peak point and/or a contact pressure value MP of a maximum peak point. Further, the measurer 330 may further extract, as features, contact pressure values SP and DP located to the left and right of the contact pressure value MP of the maximum peak point and having a predetermined ratio (e.g., 0.5 to 0.7) to the contact pressure value M P.

The measurer 330 may measure bio-information by using the extracted features. For example, in the case of measuring blood pressure, the measurer 330 may determine the contact pressure value MP of the maximum peak point, which is extracted from the oscillometric waveform, to be mean arterial pressure (MAP). Further, the measurer 330 may determine, as systolic blood pressure (SBP), a contact pressure value SP located to the right of the contact pressure value MP of the maximum peak point within a predetermined ratio range; and may determine, as diastolic blood pressure (DBP), a contact pressure value DP located to the left of the contact pressure value MP of the maximum peak point predetermined ratio range.

In another example, upon extracting one or more features from the oscillometric waveform, the measurer 330 may measure bio-information by using a predefined measurement model as represented by the following Equation 1.

$$y=ax+b \qquad \text{[Equation 1]}$$

Herein, y denotes bio-information to be obtained, such as DBP, SBP, and MAP; x denotes the extracted feature value; and a and b denote values calculated in advance through preprocessing, and may be defined differently according to the types of bio-information (e.g., DBP, SBP, and MAP). However, the measurement model is not limited thereto, and may be pre-generated in table form in which feature values and blood pressure values are mapped to each other.

Figure 5:
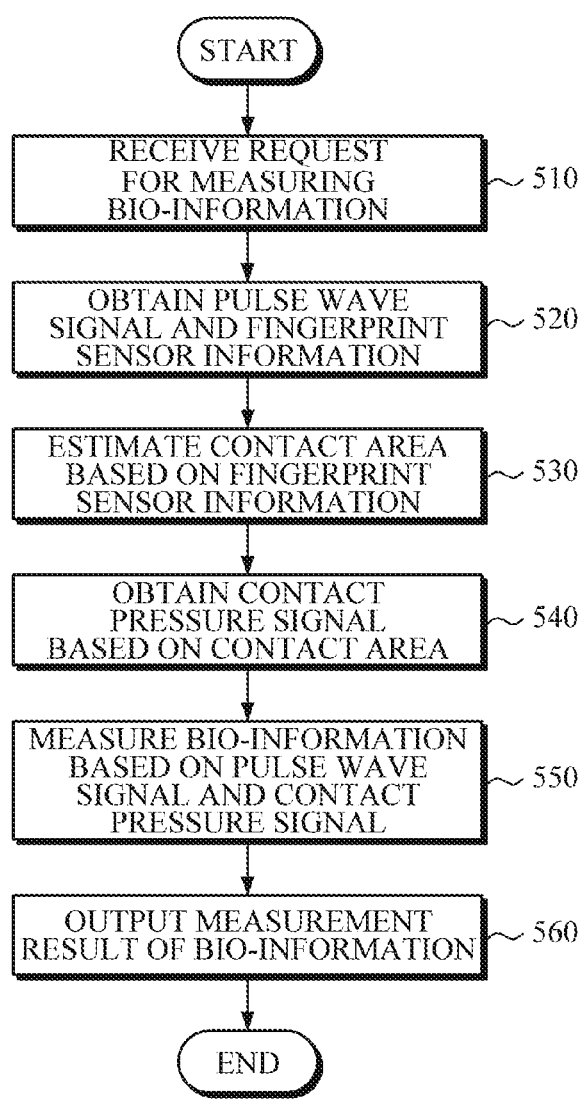
FIG. 5 is a flowchart illustrating a bio-information measuring method according to an exemplary embodiment.

FIG. 5 is a flowchart illustrating a bio-information measuring method according to an exemplary embodiment.

The bio-information measuring method of FIG. 5 is an example of a bio-information measuring method performed by the bio-information measuring apparatus 100, which is described above, such that the description thereof will be briefly made in order to avoid redundancy.

The bio-information measuring apparatus 100 may receive a request for measuring bio-information in operation 510. The request for measuring bio-information may be input from a user, or may be received from an external device connected through communication networks. However, the request for measuring bio-information is not limited thereto, and it may be determined automatically at predetermined intervals that the request for measuring bio-information is received.

Then, the bio-information measuring apparatus 100 may measure a pulse wave signal from an object during a predetermined period of time by using a pulse wave sensor 111, and at the same time, may obtain fingerprint sensor information by using the fingerprint sensor 112 in operation 520. The pulse wave sensor 111 may include one or more light sources and one or more detectors. The fingerprint sensor 112 may be a capacitive fingerprint sensor. During the measurement, a user may gradually increase or decrease contact pressure between the object and the sensor.

Then, the bio-information measuring apparatus 100 may estimate a contact area between the object and the sensors based on the fingerprint sensor information in operation 530. For example, the bio-information measuring apparatus 100 may estimate the contact area based on each pixel intensity of the fingerprint sensor 112. In particular, the bio-information measuring apparatus 100 may calculate a statistical value of each pixel intensity, and may calculate the contact area by substituting the calculated statistical value in a contact area conversion function. In particular, the contact area conversion function may be defined in various forms, such as a linear/non-linear combination function, and the like.

Subsequently, the bio-information measuring apparatus 100 may obtain a contact pressure signal between the object and the pulse wave sensor 111 based on the estimated contact area in operation 540. As described above, there is a correlation between the contact area and the contact pressure, and a contact pressure conversion function may be predefined, which represents the correlation between the contact area and the contact pressure. Upon estimating the contact area, the bio-information measuring apparatus 100 may calculate contact pressure by substituting the contact area in the contact pressure conversion function.

Next, the bio-information measuring apparatus 100 may measure bio-information based on the pulse wave signal and the contact pressure signal in operation 550. For example, the bio-information measuring apparatus 100 may measure bio-information based on the oscillometric method as described above.

Then, the bio-information measuring apparatus may provide a measurement result of bio-information to a user by using various output devices in operation 560. In particular, the output devices may include a display module to visually output the result, a speaker module to output the result through voice, a haptic module to output the result through vibration or tactile sensation, and the like.

Figure 6:
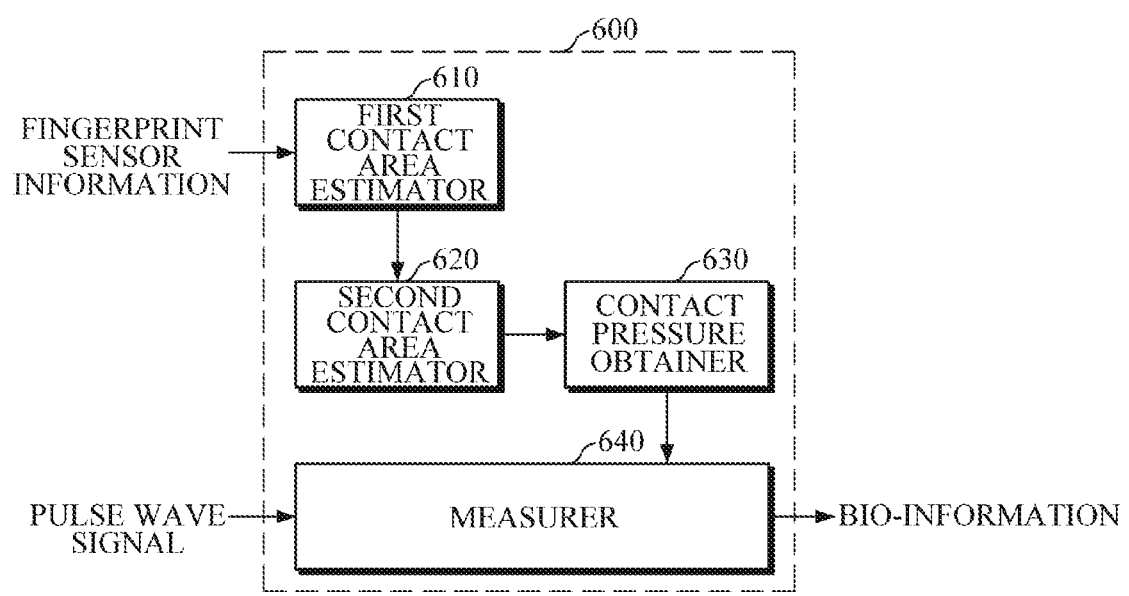
FIG. 6 is a diagram illustrating another example of a configuration of the processor of FIG. 1.
Figure 7A:
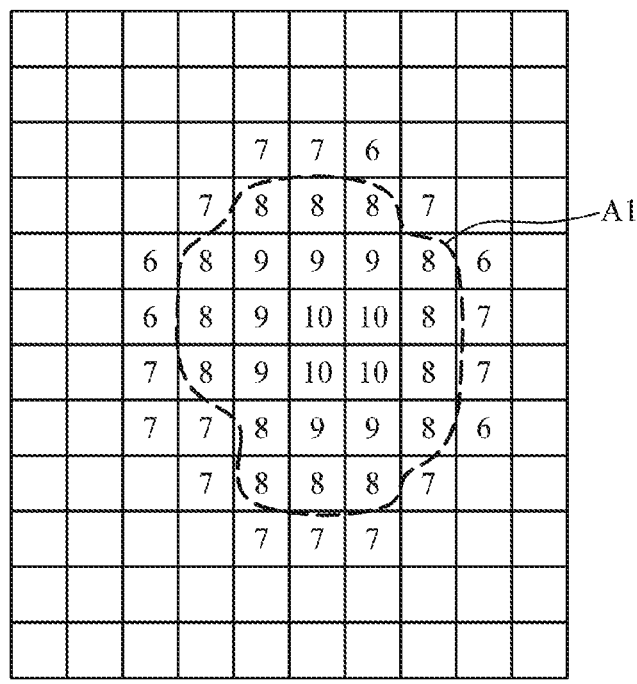

FIG. 6 is a diagram illustrating another example of a configuration of the processor of FIG. 1. FIGS. 7A and 7B are diagrams explaining an example of estimating a contact area according to the example of FIG. 6.

Referring to FIG. 6, the processor 600 according to an exemplary embodiment includes a first contact area estimator 610, a second contact area estimator 620, a contact pressure obtainer 630, and a measurer 640.

The first contact area estimator 610 may calculate a first contact area between an object and the fingerprint sensor 112 at two or more time points based on fingerprint sensor information. The first contact area estimator 610 may linearly combine pixel intensity values which are equal to or higher than a predetermined threshold at a first time point, and may determine the result to be the first contact area for the first time point. Further, the first area estimator 610 may linearly combine pixel intensity values which are equal to or higher than a predetermined threshold at a second time point, and may determine the result to be the first contact area for the second time point.

For example, FIGS. 7A and 7B illustrate pixel intensity values of the fingerprint sensor 112 which are obtained at the first time point and at the second time point when a user gradually increases contact pressure during a predetermined period of time while a user's object touches the fingerprint sensor 112. For convenience of explanation, pixel intensity values of some portions of the fingerprint sensor 112 are omitted.

Referring to FIG. 7A, the first contact area estimator 610 may determine an area A1 of pixels having intensity values equal to or higher than a predetermined threshold value (e.g., a value of 8) at the first time point, and may estimate the first contact area for the determined area A1. Referring to FIG. 7B, the first contact area estimator 610 may determine an area A2 of pixels having intensity values equal to or higher than a predetermined threshold (e.g., a value of 8) at the second time point, and may estimate the first contact area for the determined area A2. For example, in the case in which a contact area is defined to be a value obtained by adding up the pixel intensity values, the contact area at the first time point is 215 and the contact area at the second time point is 818.

The first contact area estimator 610 may preset, as a threshold value, a statistical value obtained using all pixel intensities of the fingerprint sensor 112 which are obtained at a reference time point. For example, the first contact area estimator 610 may set an average of all pixel intensities as a threshold value. However, an example of the statistical value is not limited to an average. In the case in which the first time point is the reference time point, the first contact area estimator 610 may first calculate an average of all pixel intensities, may set the calculated average as a threshold value, and then may calculate the first contact area for the first time point by using the set threshold value.

The second contact area estimator 620 may estimate a second contact area based on a change between the first contact areas calculated at two or more time points by the first contact area estimator 610. In particular, the second contact area may be an actual contact area between the object and the sensor part 110. For example, the second contact area estimator 620 may estimate the second contact area by substituting the change between the first contact areas, e.g., a difference value between the first contact area of the first time point and the first contact area of the second time point, an increasing/decreasing rate of the first contact area, and the like, in a predefined contact area conversion function. The second contact area may represent a change in the contract area between the pulse wave sensor 111 and the object while the pulse wave sensor 111 is measuring the pulse wave signal.

Once the second contact area is estimated, the contact pressure obtainer 630 may obtain a contact pressure signal from the second contact area. As described in detail above, the contact pressure obtainer 630 may obtain contact pressure from the second contact area by using the predefined contact pressure conversion function.

The measurer 640 may measure bio-information based on the pulse wave signal and the contact pressure signal. As described above, the measurer 640 may obtain the oscillometric waveform by using the pulse wave signal and the contact pressure signal, and may measure bio-information, such as blood pressure, based on the oscillometric method by extracting features from the obtained oscillometric waveform.

Figure 8:
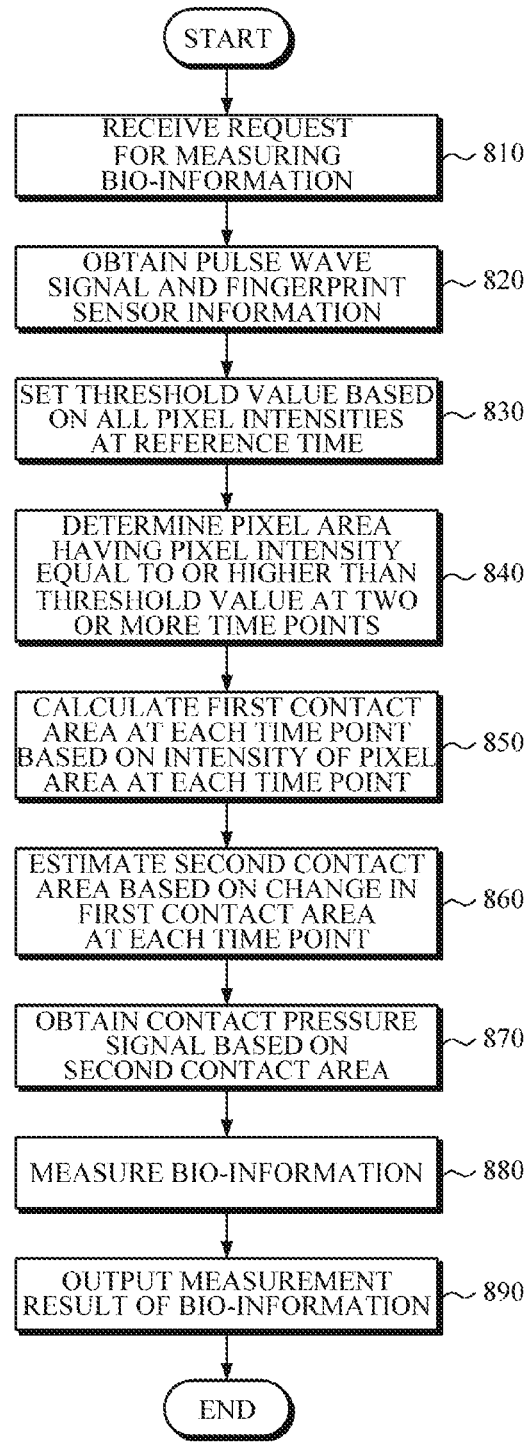
FIG. 8 is a flowchart illustrating a bio-information measuring method according to an exemplary embodiment.

FIG. 8 is a flowchart illustrating a bio-information measuring method according to an exemplary embodiment.

The bio-information measuring method of FIG. 8 is another example of a bio-information measuring method performed by the bio-information measuring apparatus 100, which is described above with reference to FIGS. 1 and 6, such that detailed description thereof will be omitted.

Upon receiving a request for measuring bio-information in operation 810, the bio-information measuring apparatus 100 may obtain a pulse wave signal and fingerprint sensor information by using the pulse wave sensor 111 and the fingerprint sensor 112 respectively during a predetermined period of time in operation 820.

Then, the bio-information measuring apparatus 100 may set a threshold value based on all pixel intensities at a reference time in operation 830. The bio-information measuring apparatus 100 may set, as the threshold value, a statistical value, e.g., an average, of all pixel intensities at the reference time. In the case in which there is a preset threshold value, the operation 830 may be omitted.

Subsequently, based on the fingerprint sensor information, the bio-information measuring apparatus 100 may determine a contact area between an object and the fingerprint sensor 112 at two or more time points in operation 840. As illustrated in FIGS. 7A and 7B, the bio-information measuring apparatus 100 may determine the areas A1 and A1 of pixels having intensities equal to or higher than a preset threshold value determined for each measurement point.

Next, the bio-information measuring apparatus 100 may calculate a first contact area at each time point based on the pixel intensities of areas determined for each time point in operation 850. For example, the bio-information measuring apparatus 100 may determine, as the first contact area for the first time point, a result obtained by adding up the pixel intensity values equal to or higher than a preset threshold value at the first time point. Similarly, the bio-information measuring apparatus 100 may determine, as the first contact area for the second time point, a result obtained by adding up the pixel intensity values equal to or higher than a preset threshold value at the second time point.

Then, the bio-information measuring apparatus 100 may estimate a second contact area based on a change between the first contact areas calculated at each time point in operation 860. For example, the bio-information measuring apparatus 100 may estimate the second contact area based on the change between the first contact areas calculated at two or more time points by applying a predefined contact area conversion function.

Subsequently, the bio-information measuring apparatus 100 may obtain a contact pressure signal based on the second contact area in operation 870. For example, a contact pressure conversion function, which represents a correlation between the contact area and the contact pressure, may be predefined, and the bio-information measuring apparatus 100 may obtain the contact pressure signal by applying the contact pressure conversion function.

Next, the bio-information measuring apparatus 100 may measure bio-information based on the pulse wave signal and the contact pressure signal in operation 880. In particular, the bio-information measuring apparatus 100 may measure bio-information based on the oscillometric method.

Then, the bio-information measuring apparatus 100 may provide a measurement result of bio-information to a user in operation 890. Various output devices may be used to effectively provide the measurement result to a user.

Figure 9:
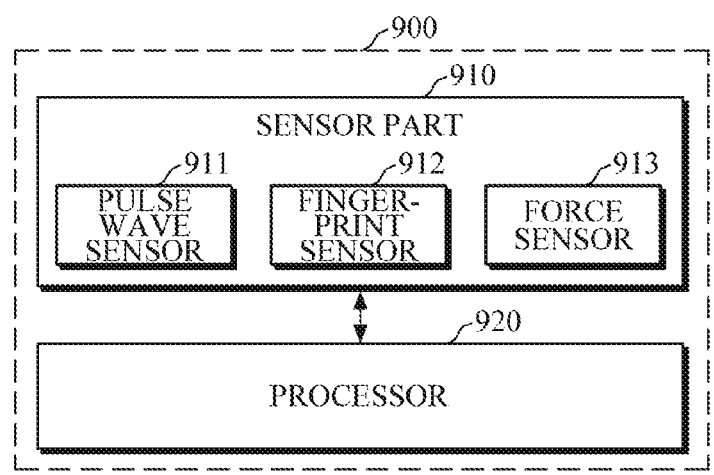
FIG. 9 is a block diagram illustrating a bio-information measuring apparatus according to an exemplary embodiment.
Figure 10:
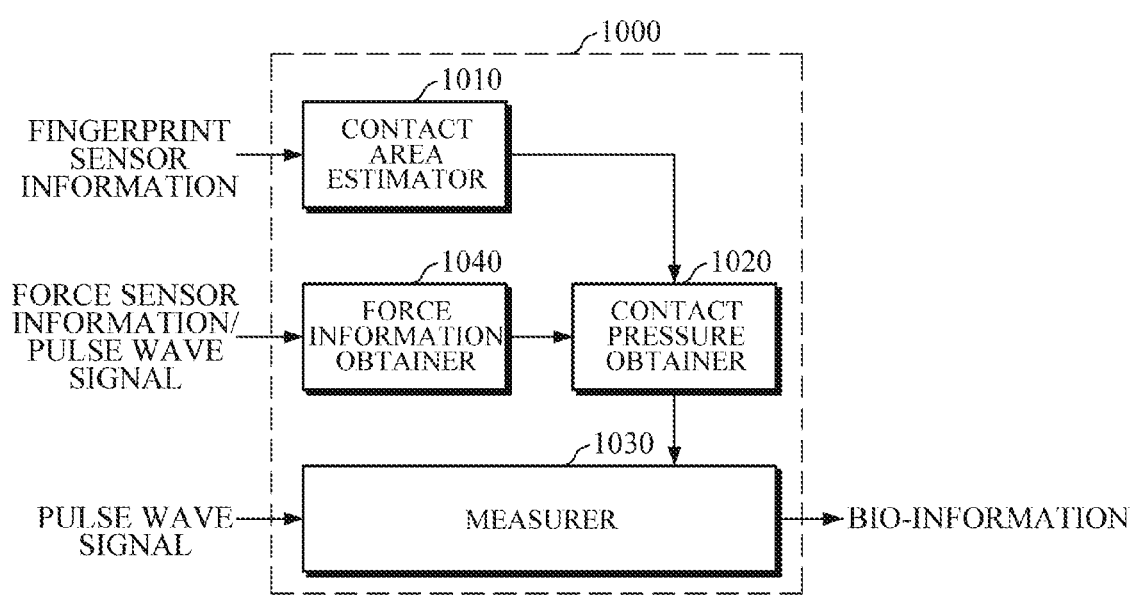
FIG. 10 is a diagram illustrating an example of a configuration of a processor of FIG. 9.

FIG. 9 is a block diagram illustrating a bio-information measuring apparatus according to an exemplary embodiment. FIG. 10 is a diagram illustrating an example of a configuration of a processor of FIG. 9.

Referring to FIG. 9, the bio-information measuring apparatus 900 according to an exemplary embodiment includes a sensor part 910 and a processor 920.

In the exemplary embodiment, the sensor part 910 may further include a force sensor 913, in addition to the pulse wave sensor 911 and the fingerprint sensor 912. The pulse wave sensor 911 and the fingerprint sensor 912 are described in detail above with reference to FIG. 1.

The force sensor 913 may be mounted on a rear surface of the pulse wave sensor 911 and/or the fingerprint sensor 912, i.e., a surface opposite to a surface that comes into contact with the object. When the object touches the pulse wave sensor 911 and the fingerprint sensor 912 and applies force thereto, the force sensor 913 may measure force information such as the intensity of force.

The processor 920 may measure bio-information based on the pulse wave signal, the fingerprint sensor information, and the force information.

Referring to FIG. 10, the processor 1000 includes a contact area estimator 1010, a contact pressure obtainer 1020, a measurer 1030, and a force information obtainer 1040. Parts with the same name as those of the aforementioned bio-information measuring apparatus 100 perform substantially the same functions, such that detailed description thereof will be omitted.

The force information obtainer 1040 may obtain information of force exerted from an object (e.g., a finger) to the sensor part 910 during measurement of pulse waves. For example, in the case in which the force sensor 913 is mounted on the sensor part 910 as illustrated in the exemplary embodiment, the force information obtainer 1040 may receive information of force measured by the force sensor 913.

In another example, in the case in which the pulse wave sensor 911 measures pulse wave signals of multiple wavelengths, the force information obtainer 1040 may obtain force information by using the measured pulse wave signals of multiple wavelengths. Accordingly, the force information obtainer 1040 may also be included in an apparatus, in which the force sensor 913 is not mounted on the sensor part 110, as in the bio-information measuring apparatus 100 described above.

The force information obtainer 1040 may obtain differential signals between a pulse wave signal of a certain wavelength and pulse wave signals of two or more different wavelengths, and may obtain the force information based on the differential signals. For example, assuming that the pulse wave signals having multiple wavelengths are pulse wave signals of green, red, and blue wavelengths, the force information obtainer 1040 may pass the pulse wave signal of each wavelength through a low pass filter (LPF), to generate a pulse wave direct current (DC) signal of each wavelength. Further, the force information obtainer 1040 may calculate a ratio between a first differential signal, obtained by subtracting a pulse wave DC signal of a blue wavelength from a pulse wave DC signal of a green wavelength, and a second differential signal, obtained by subtracting a pulse wave DC signal of a blue wavelength from a pulse wave DC signal of a red wavelength, and may determine the calculated ratio at each time point to be the intensity of force.

The contact pressure obtainer 1020 may obtain a contact pressure signal based on the obtained force information and the contact area. For example, the contact pressure obtainer 1020 may calculate the contact pressure at each time point by dividing the intensity of force at each time point by the contact area.

The measurer 1030 may measure bio-information based on the pulse wave signal and the contact pressure. As described above, the measurer 1030 may measure bio-information based on the oscillometric method. Once the pulse wave sensor 911 measures the pulse wave signal having multiple wavelengths, the measurer 1030 may select any one pulse wave signal according to various criteria, or may obtain one pulse wave signal by combining pulse wave signals of multiple wavelengths using a predefined combination model. Alternatively, the measurer 1030 may obtain oscillometric waveforms using each pulse wave signal and contact pressure, and may obtain one combined oscillometric waveform by combining the obtained oscillometric waveforms using a predefined combination model.

Figure 11:
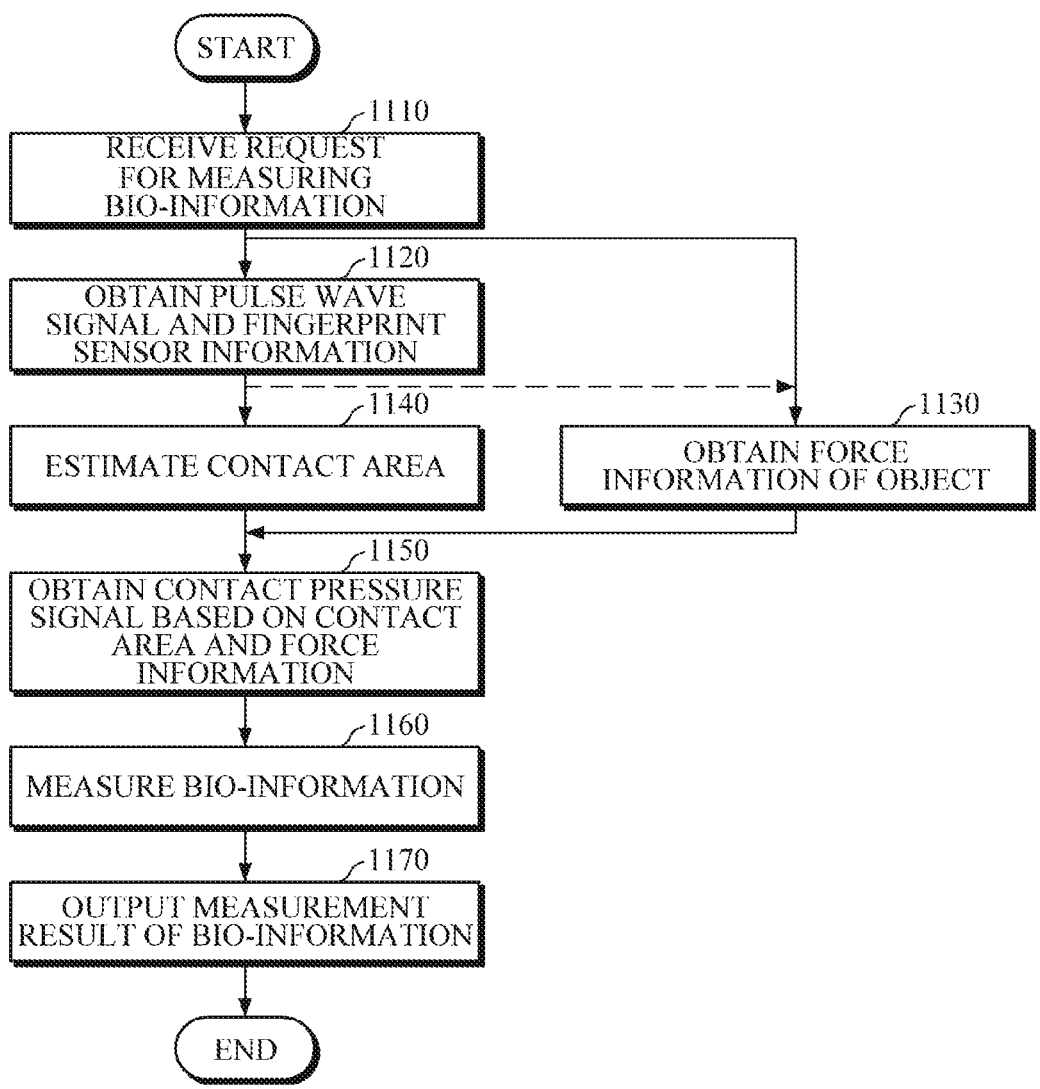
FIG. 11 is a flowchart illustrating a bio-information measuring method according to an exemplary embodiment.

FIG. 11 is a flowchart illustrating a bio-information measuring method according to an exemplary embodiment.

The bio-information measuring method of FIG. 11 may be an example of a bio-information measuring method performed by the bio-information measuring apparatus 900 of FIG. 9.

Upon receiving a request for measuring bio-information in operation 1110, the bio-information measuring apparatus 900 may obtain a pulse wave signal and fingerprint sensor information by using the pulse wave sensor 911 and the fingerprint sensor 912 respectively during a predetermined period of time in operation 1120.

Then, the bio-information measuring apparatus 900 may obtain force information, such as the intensity of force applied by the object to the force sensor 913, in operation 1130. In particular, the bio-information measuring apparatus 900 may obtain force information by using the force sensor 913 mounted in the bio-information measuring apparatus 900, in which the operations 1130 and 1120 may be performed at the same time. In the case in which the force sensor 913 is not included therein, pulse wave signals of multiple wavelengths may be measured in operation 1120, and then force information may be obtained by using the measured pulse wave signals of multiple wavelengths.

Subsequently, the bio-information measuring apparatus 900 may estimate a contact area of the object based on the fingerprint sensor information in operation 1140. For example, as described above, the bio-information measuring apparatus 900 may determine a contact area by adding up pixel intensity values of the fingerprint sensor 912 at each time point, for each time point.

Next, the bio-information measuring apparatus 900 may obtain the contact pressure signal based on the contact area and the force information in operation 1150. For example, the bio-information measuring apparatus 900 may calculate the contact pressure at each time point by dividing the intensity of force at each time point by the contact area.

Then, the bio-information measuring apparatus 900 may obtain bio-information based on the pulse wave signal and the contact pressure signal in operation 1160. In particular, the bio-information measuring apparatus 900 may obtain bio-information based on the oscillometric method.

Subsequently, the bio-information measuring apparatus 900 may provide a measurement result of bio-information to a user in operation 1170. Various output devices may be used to effectively provide the measurement result to a user.

Figure 12:
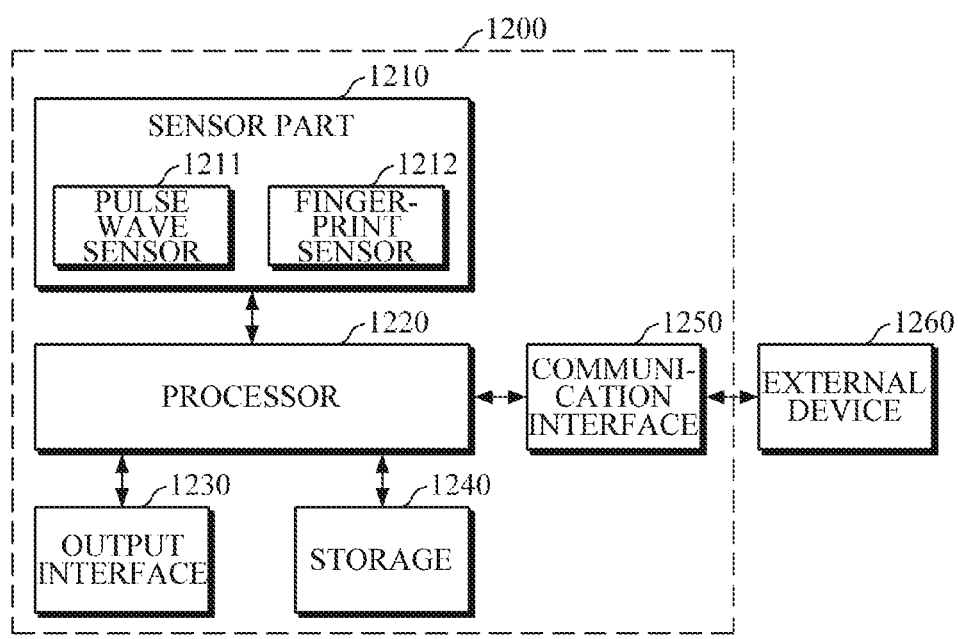
FIG. 12 is a block diagram illustrating a bio-information measuring apparatus according to an exemplary embodiment.
Figure 13:
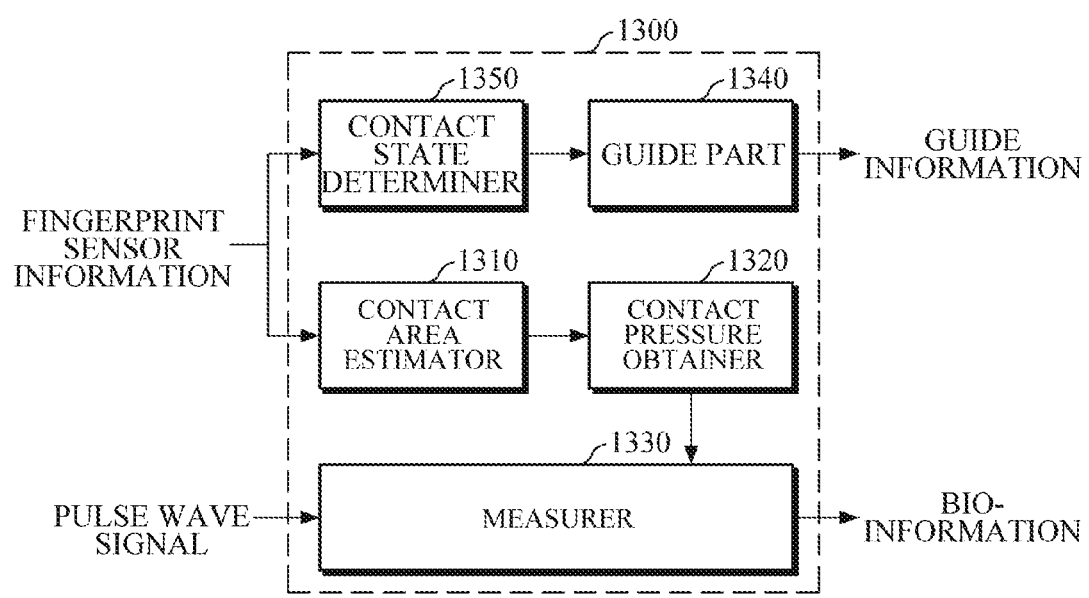
FIG. 13 is a diagram illustrating an example of a configuration of a processor of FIG. 12.
Figure 14:
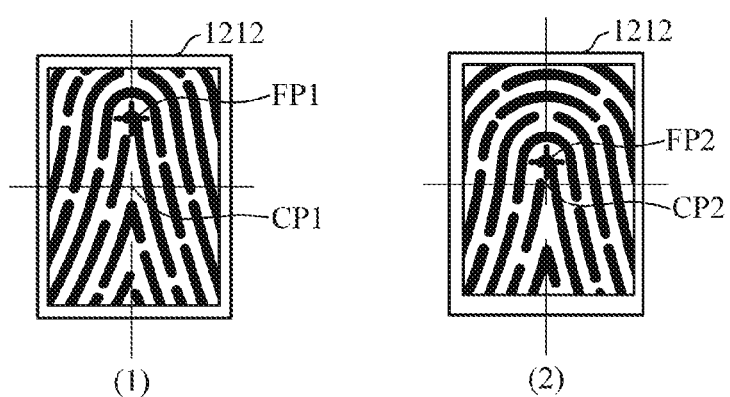
FIG. 14 is a diagram explaining a method of determining a contact state.

FIG. 12 is a block diagram illustrating a bio-information measuring apparatus according to an exemplary embodiment. FIG. 13 is a diagram illustrating an example of a configuration of a processor of FIG. 12. FIG. 14 is a diagram explaining a method of determining a contact state.

Referring to FIG. 12, the bio-information measuring apparatus 1200 according to an exemplary embodiment includes a sensor part 1210, a processor 1220, an output interface 1230, a storage 1240, and a communication interface 1250. Detailed description of parts with the same name, which are described above, will be omitted.

The sensor part 1210 includes a pulse wave sensor 1211 and a fingerprint sensor 1212. In addition, the sensor part 1210 may further include a force sensor 913.

The processor 1220 may measure bio-information based on the pulse wave signal and the fingerprint sensor information received from the sensor part 1210.

FIG. 13 illustrates an example of the processor 1220 of FIG. 12. Referring to FIG. 13, the processor 1300 includes a contact area estimator 1310, a contact pressure obtainer 1320, a measurer 1330, a guide part 1340, and a contact state determiner 1350.

The contact area estimator 1310 may estimate a contact area of an object based on the fingerprint sensor information. The contact pressure obtainer 1320 may obtain a contact pressure signal, corresponding to the contact area, based on information about the estimated contact area. In particular, the contact pressure obtainer 1320 may obtain the contact pressure signal directly from the contact area. Alternatively, the contact pressure obtainer 1320 may obtain the contact pressure by using the contact area along with the force information obtained using pulse wave signals of multiple wavelengths received from the force sensor 913.

The measurer 1350 may measure bio-information based on the oscillometric method by using the pulse wave signal and the contact pressure signal.

Upon receiving a request for measuring bio-information, the guide part 1340 may generate guide information for guiding a user's object to accurately touch the sensor part 1210, and may output the guide information through the output interface 1230. In particular, the guide information may include a contact position of the object on the sensor part 1210, and information on the intensity of pressure to be applied by the object to the sensor part 1210 during measurement.

The guide part 1340 may generate guide information appropriate for a user, by referring to various types of information stored in the storage 1240. For example, by using various types of information such as a user's gender, age, health state information, a measurement history of bio-information, an appropriate contact position and pressure for each object (e.g., finger, wrist, etc.), an appropriate contact intensity for each measurement time, and the like, the guide part 1340 may generate guide information such as an optimal contact position or contact pressure for a current user.

When a user's object touches the sensor part 1210 by referring to the guide information, the contact state determiner 1350 may determine a contact state between the object and the sensor part 1210. For example, FIG. 14 illustrates a fingerprint image of a touching finger to measure a pulse wave signal. The contact state determiner 1350 extracts a fingerprint feature point from the fingerprint image, and may determine a contact state based on a distance between the extracted fingerprint feature point and a specific position of the fingerprint sensor 1212. In particular, the fingerprint feature point may be a center position of the object, and the specific position of the fingerprint sensor 1212 may be a center position of the fingerprint sensor 1212.

Referring to FIG. 14, fingerprint image (1) of FIG. 14 illustrates a case in which a distance between a center position FP1 of the fingerprint image and a center position CP1 of the fingerprint sensor 1212 is relatively long (e.g., the distance is greater than or equal to a predetermined value); and fingerprint image (2) of FIG. 14 illustrates a case in which a distance between the center position FP2 of the fingerprint image and a center position CP2 of the fingerprint sensor 1212 is relatively short (e.g., the distance is less than the predetermined value). The contact state determiner 1350 calculates a distance between the center position of the object on the fingerprint image and the center position of the fingerprint sensor 1212, and/or a direction. In the case in which the calculated distance falls outside of a predetermined threshold value, or a direction is not a predetermined direction, the contact state determiner 1350 may determine that the contact state is not normal, but the determination of contact state is not limited thereto.

In response to determination that the contact state is not normal, the guide part 1340 may generate guide information for guiding a user to change a contact position or a contact intensity, and may output the guide information to a user. The contact state determiner 1350 may continuously determine the contact state during measurement of pulse wave signals.

Referring back to FIG. 12, the output interface 1230 may output a pulse wave signal and fingerprint sensor information which are obtained by the sensor part 120, and/or a processing result of the processor 1220. In particular, the output interface 1230 may visually provide various types of information through a display. Alternatively, the output interface 120 may provide various types of information in a non-visual manner, such as voice, vibration, tactile sensation, and the like, by using a speaker module, a haptic module, and the like.

The storage 1240 may store various types of reference information. In particular, the reference information may include user information such as a user's age, gender, health state, and the like. Further, the reference information may include information required for measuring bio-information, such as guide information on a contact state, a contact area conversion function, a contact pressure conversion function, a measurement model, calibration reference information, and the like. However, the reference information is not limited thereto, and the storage 1240 may further store various results processed by the processor 1220.

The storage 1240 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Once bio-information is measured, the processor 1220 may determine whether to calibrate a bio-information measurement value based on predetermined criteria for determination of calibration. In particular, the criteria for determination may be predetermined by selecting one, or a combination of two or more, of a normal range of bio-information measurement values, a number of times the measurement values continuously fall outside the normal range, a total number of times the measurement values fall outside the normal range during a predetermined period of time, a state change of an object, and a health state of a user.

Upon determination to calibrate a measurement value, the processor 1220 may calibrate bio-information by calibrating a bio-information measurement value by using reference information for calibration stored in the storage 1240. In particular, the reference information for calibration may include an actual bio-information measurement value (e.g., cuff blood pressure), and offset value, and the like.

The communication interface 1250 may communicate with various external devices 1260 by wire and wirelessly. Examples of the external device 1260 may include various devices having a function of measuring bio-information, such an information processing device such as a smartphone, a tablet PC, a desktop PC, and the like, and a cuff blood pressure measuring apparatus. The communication interface 1250 may communicate with the external device 1260 by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WiFi communication, Radio Frequency Identification (RFID) communication, 3G communication, 4G communication, 5G communication, and the like. However, this is merely exemplary and is not intended to be limiting.

Figure 15:
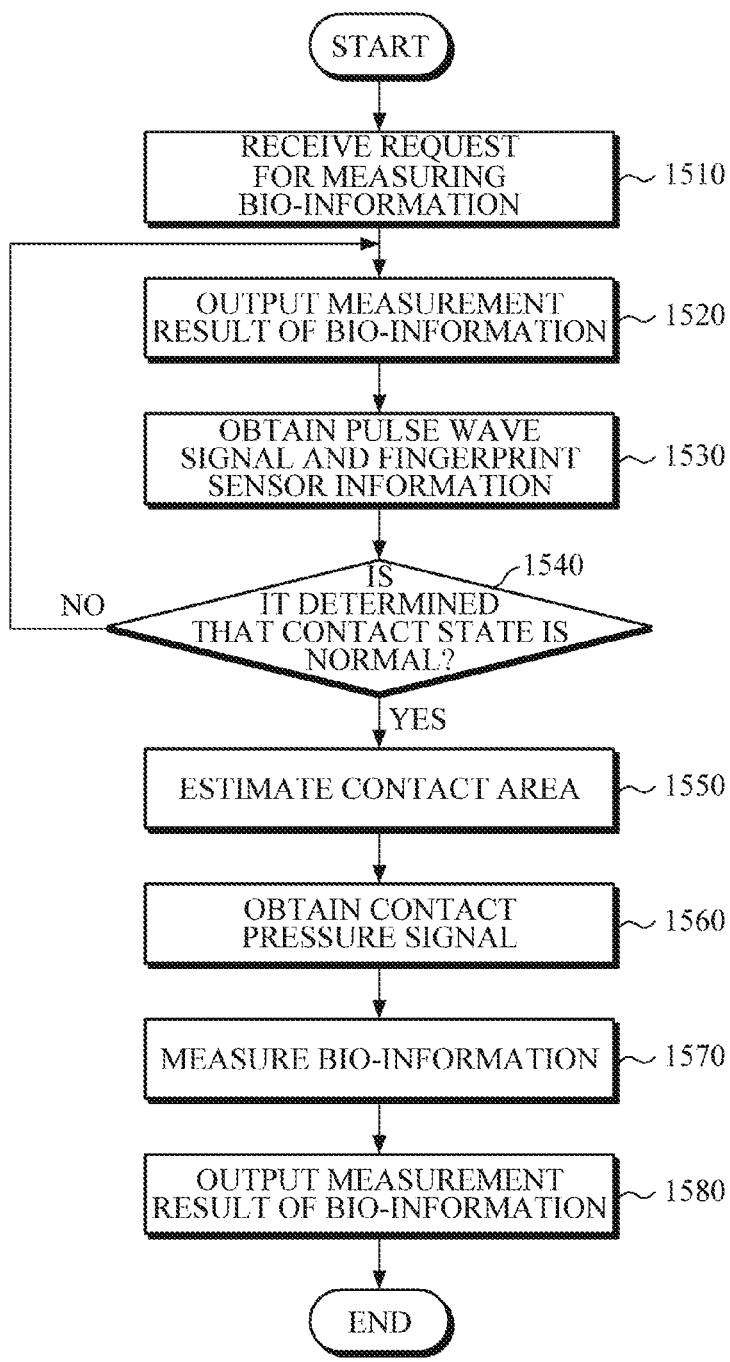
FIG. 15 is a flowchart illustrating a bio-information measuring method according to an exemplary embodiment.

FIG. 15 is a flowchart illustrating a bio-information measuring method according to an exemplary embodiment.

The bio-information measuring method of FIG. 15 may be an example of a bio-information measuring method performed by the bio-information measuring apparatus 1200 of FIG. 12.

The bio-information measuring apparatus 1200 may receive a request for measuring bio-information in operation 1510.

Then, the bio-information measuring apparatus 1200 may output guide information for measuring a contact intensity and/or contact pressure of an object in operation 1520.

Subsequently, the bio-information measuring apparatus 1200 may obtain a pulse wave signal and fingerprint sensor information by using the pulse wave sensor 1211 and the fingerprint sensor 1212 respectively during a predetermined period of time in operation 1530.

Next, the bio-information measuring apparatus 1200 may determine whether a contact state is normal based on the fingerprint sensor information in operation 1540. For example, the bio-information measuring apparatus 1200 may extract a fingerprint feature point from a fingerprint image, and may determine whether a contact state is normal based on the extracted fingerprint feature point and a specific position of the fingerprint sensor 1212. In particular, the fingerprint feature point may be a center position of the object, and the specific position of the fingerprint sensor 1212 may be a center position of the fingerprint sensor. The bio-information measuring apparatus 1200 may calculate a distance between the center position of the object on the fingerprint image and the center position of the fingerprint sensor 1212; and in the case in which the calculated distance falls outside of a predetermined threshold value, the bio-information measuring apparatus 1200 may determine that the contact state is not normal.

Then, upon determining in 1540 that the contact state is not normal, the bio-information measuring apparatus 1200 may return to 1520 to guide a user to change a contact position or a contact intensity. For example, the bio-information measuring apparatus 1200 may guide a user to move to a center position of the fingerprint sensor 1212 based on the distance between the center position of the object and the center position of the fingerprint sensor 1212, and direction information.

Subsequently, upon determining in operation 1540 that the contact state is normal, the bio-information measuring apparatus 1200 may estimate a contact area of the object based on the fingerprint sensor information in operation 1550. For example, the bio-information measuring apparatus 1200 may calculate a contact area by substituting a statistical value of each pixel intensity of the fingerprint sensor 1212 in a predefined contact area conversion function.

Next, the bio-information measuring apparatus 1200 may obtain a contact pressure signal between the object and the pulse wave sensor 1211 from the estimated contact area in operation 1560. For example, by applying a contact pressure conversion function that represents a correlation between the contact area and the contact pressure, the bio-information measuring apparatus 1200 may directly obtain a contact pressure signal from the contact area. Alternatively, in the case in which a force sensor 913 is mounted on the sensor part 1210, the bio-information measuring apparatus 1200 may obtain the contact pressure based on force information measured by the force sensor 913, and the contact area. In addition, the bio-information measuring apparatus 1200 may obtain force information from pulse wave signals of multiple wavelengths, which are obtained by the pulse wave sensor 1211, and may obtain the contact pressure based on the obtained force information and the contact area.

Then, the bio-information measuring apparatus 1200 may obtain bio-information based on the pulse wave signal and the contact pressure signal in operation 1570. For example, the bio-information measuring apparatus 1200 may obtain bio-information based on the oscillometric method.

Subsequently, the bio-information measuring apparatus 1200 may provide a measurement result of bio-information to a user in operation 1580.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-information measuring apparatus, comprising:
   a pulse wave sensor configured to measure a pulse wave signal from an object;
   a fingerprint sensor configured to obtain fingerprint information of the object; and
   a processor configured to calculate a statistical value of pixel intensities included in the fingerprint information, estimate a size of a contact area between the object and the pulse wave sensor based on the statistical value by applying a predefined contact area conversion function to the statistical value, and obtain bio-information based on the pulse wave signal and the contact area,
   wherein the processor is further configured to determine a contact pressure between the pulse wave sensor and the object based on the size of the contact area, and to obtain an oscillometric waveform based on the pulse wave signal and the contact pressure, and obtain the bio-information based on the oscillometric waveform, and
   wherein the statistical value of pixel intensities corresponds to a simple sum, a weighted sum, an average, or a median value of the pixel intensities.

2. The bio-information measuring apparatus of claim 1, wherein the pulse wave sensor comprises:
   a light source configured to emit light onto the object; and
   a detector configured to detect the light that is reflected from the object after being emitted to the object.

3. The bio-information measuring apparatus of claim 1, wherein the fingerprint sensor is a capacitive fingerprint sensor.

4. The bio-information measuring apparatus of claim 1, wherein the processor is further configured to determine the contact pressure based on the size of the contact area by applying a predefined contact pressure conversion function.

5. The bio-information measuring apparatus of claim 1, wherein the bio-information comprises at least one of blood pressure, vascular age, degree of arteriosclerosis, aortic pressure waveform, vascular compliance, stress index, and degree of fatigue.

6. The bio-information measuring apparatus of claim 1, wherein the processor is further configured to determine a change in the contact area between the pulse wave sensor and the object while the pulse wave signal is being measured, and obtain the bio-information based on the pulse wave signal and the change in the contact area.

7. The bio-information measuring apparatus of claim 6, wherein the fingerprint information comprises the pixel intensities, and
   wherein the processor is further configured to estimate the contact area by linearly combining one or more of the pixel intensities which are equal to or higher than a predetermined threshold value.

8. A bio-information measuring method, comprising:
   obtaining a pulse wave signal from an object by using a pulse wave sensor;
   obtaining fingerprint information of the object;
   calculating a statistical value of pixel intensities included in the fingerprint information;
   estimating a size of a contact area between the object and the pulse wave sensor based on the statistical value by applying a predefined contact area conversion function to the statistical value;
   determining a contact pressure between the object and the pulse wave sensor based on the size of the contact area; and
   obtaining bio-information based on the pulse wave signal and the size of the contact area,
   wherein the obtaining the bio-information comprises obtaining an oscillometric waveform based on the pulse wave signal and the contact pressure; and obtaining the bio-information based on the oscillometric waveform, and
   wherein the statistical value of pixel intensities corresponds to a simple sum, a weighted sum, an average, or a median value of the pixel intensities.

9. The bio-information measuring method of claim 8, wherein the determining the contact pressure comprises determining the contact pressure based on the contact area by applying a predefined contact pressure conversion function.

10. The bio-information measuring method of claim 8, further comprising:
    determining a change in the contact area between the pulse wave sensor and the object while obtaining the pulse wave signal,
    wherein the obtaining the bio-information comprises obtaining the bio-information based on the pulse wave signal and the change in the contact area.

11. The bio-information measuring method of claim 10, wherein the fingerprint information comprises a fingerprint image, and
    wherein the estimating the contact area comprises:
    determining pixels of the fingerprint image which have the pixel intensities equal to or higher than a predetermined threshold value; and
    estimating the contact area by linearly combining the pixel intensities of the determined pixels.

* * * * *